United States Patent [19]

Neumann et al.

[11] Patent Number: 5,554,318
[45] Date of Patent: Sep. 10, 1996

[54] USE OF COMPOUNDS WHICH ABSORBS AND FLUORESCE IN THE IR RANGE AS CRACK-DETECTING AGENTS

[75] Inventors: Peter Neumann, Mannheim; Jürgen Kipper, Karlsruhe; Bernhard Albert, Maxdorf; Gerhard Wagenblast, Wachenheim, all of Germany

[73] Assignee: BASF Aktiengesellschaft, Ludwigshafen, Germany

[21] Appl. No.: 379,283

[22] Filed: Jan. 27, 1995

[30] Foreign Application Priority Data

Feb. 7, 1994 [DE] Germany ............... 44 03 664.7

[51] Int. Cl.⁶ .................................. G01N 21/91
[52] U.S. Cl. .............. 252/301.19; 427/8; 73/36
[58] Field of Search ............ 252/301.19; 427/8; 73/36

[56] References Cited

U.S. PATENT DOCUMENTS

| | | | |
|---|---|---|---|
| 3,484,467 | 12/1969 | Susi et al. | 260/440 |
| 3,560,399 | 2/1971 | Irsak | 252/301.19 |
| 3,679,598 | 7/1972 | Alburger | 252/301.19 |
| 3,708,665 | 1/1973 | Prine | 250/71 T |
| 3,958,119 | 5/1976 | Shigekawa | 250/302 |
| 4,191,048 | 3/1980 | Molina | 73/104 |
| 4,990,649 | 2/1991 | Schrott, et al. | 560/25 |
| 5,336,714 | 8/1994 | Krutak et al. | 252/301.19 |

FOREIGN PATENT DOCUMENTS

| | | |
|---|---|---|
| 0155780 | 9/1985 | European Pat. Off. . |
| 0310080 | 4/1989 | European Pat. Off. . |
| 0336213 | 10/1989 | European Pat. Off. . |
| 0358080B1 | 12/1993 | European Pat. Off. . |
| 0464543B1 | 8/1994 | European Pat. Off. . |
| 1073739 | 4/1960 | Germany . |
| 3305146 | 4/1984 | Germany . |
| 2168372 | 6/1986 | United Kingdom . |
| 2200650 | 10/1990 | United Kingdom . |

OTHER PUBLICATIONS

Bob L. Wheeler, et al., "A Silicon Phthalocyanine and a Silicon Naphthalocyanine: Synthesis, Electrochemistry, and Electrogenerated Chemiluminescence", J. Am. Chem. Soc., 1984, pp. 7404–7410.

*Primary Examiner*—Melissa Bonner
*Attorney, Agent, or Firm*—Oblon, Spivak, McClelland, Maier, & Neustadt, P.C.

[57] ABSTRACT

Compounds from the class consisting of the phthalocyanines, naphthalocyanines, the aminium compounds of aromatic amines, the methine dyes or the azulenesquaric acid dyes, which have their absorption maximum in the range from 600 to 1,200 nm and a fluorescence maximum in the range from 620 to 1,200 nm, are used as crack-detecting agents.

5 Claims, No Drawings

USE OF COMPOUNDS WHICH ABSORBS AND FLUORESCE IN THE IR RANGE AS CRACK-DETECTING AGENTS

The present invention relates to the use of compounds from the class consisting of the metal-free or metal-containing phthalocyanines, the metal-free or metal-containing naphthalocyanines, the aminium compounds of aromatic amines, the methine dyes or the azulenesquaric acid dyes, which have their absorption maximum in the range from 600 to 1,200 nm and a fluorescence maximum in the range from 620 to 1,200 nm, as crack-detecting agents.

Visible fluorescent dyes frequently used for detecting material defects, in particular cracks, in the production of workpieces or in the testing of important components, for example aircraft wings or turbine parts. The excitation light source used is in general a UV lamp.

For example, U.S. Pat. No. 3,679,598 describes mixtures of fluorescent dyes with further components, for example benzophenones, for detecting very small cracks in test objects.

According to U.S. Pat No. 3,560,399, dry developers based on silica gel, aluminum silicates or kaolin should be used for increasing the sensitivity of detection of the fluorescence at cracks.

Finally, U.S. Pat No. 3,958,119 describes a method by means of which the efficiency of the fluorescent dyes as crack-detecting agents is to be assessed.

The short-wavelength light sources used in the prior art, for example UV lamps, are expensive and have very large dimensions compared with the cracks investigated.

It is an object of the present invention to provide suitable compounds which can be used as crack-detecting agents. The crack-detecting agents should have sufficiently strong fluorescence in the near infrared, permitting the detection of the fluorescence by means of commercial apparatuses after excitation with a suitable simple radiation source.

We have found that this object is achieved and that the compounds defined at the outset can advantageously be used as crack-detecting agents.

Metal-containing phthalocyanines or naphthalocyanines generally have lithium (two atoms) magnesium, zinc, manganese, VO, TiO, AlCl or disubstituted silicon as the central atom. Suitable phthalocyanines are, for example, of the formula Ia

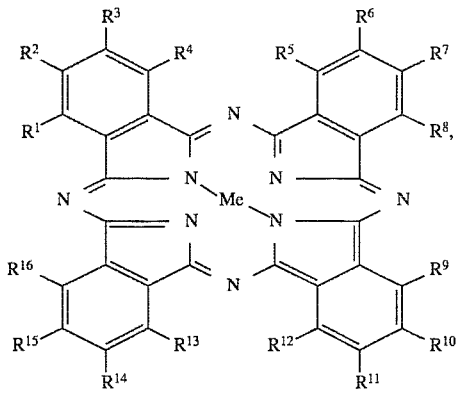

where

Me is two hydrogen atoms, two lithium atoms, magnesium, zinc, manganese, VO, TiO, AlCl or a radical of the formula

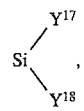

where $Y^{17}$ and $Y^{18}$ independently of one another are each hydroxyl, $C_1$–$C_{20}$-alkoxy, $C_1$–$C_{20}$-alkyl, $C_2$–$C_{20}$-alkenyl, $C_3$–$C_{20}$-alkenyloxy or a radical of the formula

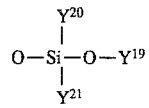

where $Y^{19}$ is $C_1$–$C_{20}$-alkyl, $C_2$–$C_{20}$-alkenyl or $C4C$–$C20$-alkadienyl and $Y^{20}$ and $Y^{21}$ independently of one another are each $C_1$–$C_{12}$-alkyl, $C_2$–$C_{12}$-alkenyl or the abovementioned radical $OY^{19}$, at least 4 of the radicals $R^1$ to $R^{16}$ independently of one another are each a radical of the formula $W$—$X^1$, where W is a chemical bond, oxygen, sulfur, imino, $C_1$–$C_4$-alkylimino or phenylimino and $X^1$ is $C_1$–$C_{20}$-alkyl which may be interrupted by 1 to 4 oxygen atoms as ether functions and may be substituted by phenyl, or $X^1$ is adamantyl, $C_5$–$C_7$-cycloalkyl or unsubstituted or substituted phenyl, and any remaining radicals $R^1$ to $R^{16}$ are each hydrogen, halogen, hydroxysulfonyl or $C_1$–$C_4$-dialkylsulfamoyl.

Other suitable phthalocyanines are, for example, the formula Ib

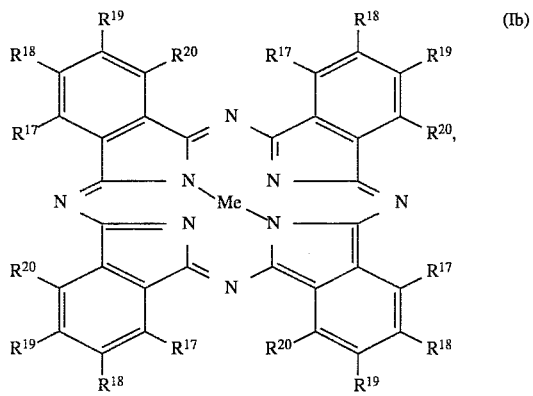

where $R^{17}$ and $R^{is}$ or $R^{is}$ and $R^{19}$ or $R^{19}$ and $R^{20}$ together in each case form a radical of the formula $X^2$-$C_2H_4$-$X^3$, where one of the two radicals $X^2$ and $X^3$ is oxygen and the other is imino or $C_1$–$C_4$-alkylimino, and $R^{19}$ and $R^{20}$ or $R^{17}$ and $R^{20}$ or $R^{17}$ and $R^{18}$ independently of one another are in each case hydrogen or halogen and Me has the abovementioned meaning.

Suitable naphthalocyanines are, for example, of the formula II

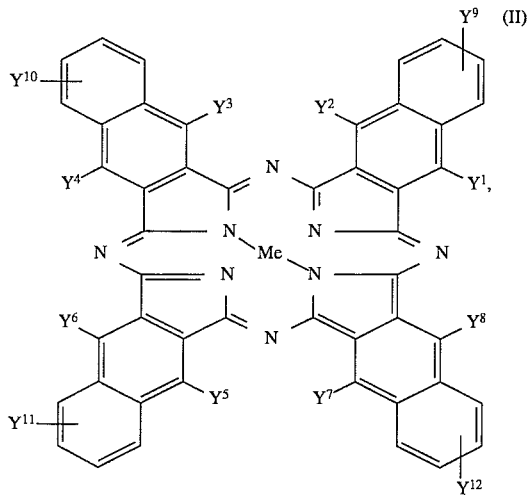

(II)

where y$^1$, Y$^2$, Y$^3$, Y$^4$, Y$^6$, Y$^7$ and Y$^8$ independently of one another are each hydrogen, hydroxyl or a radical of the formula W—X$^4$, where W is a chemical bond, oxygen, sulfur, imino, C$_1$–C$_4$-alkylimino or phenylimino and X$^4$ is C$_1$–C$_{20}$-alkyl, which may be interrupted by 1 to 4 oxygen atoms as ether functions and may be substituted by phenyl, or X$^4$ is C$_5$–C$_7$-cycloalkyl, C$_2$–C$_{20}$-alkenyl or C$_4$–C$_{20}$-alkadienyl, and Y$^9$, Y$^{10}$, Y$^{11}$ and Y$^{12}$ independently of one another are each hydrogen, C$_1$–C$_{20}$-alkyl or C$_1$–C$_{20}$-alkoxy, where the alkyl groups may each be interrupted by 1 to 4 oxygen atoms as ether functions, or are each halogen, hydroxysulfonyl or C$_1$–C$_4$-dialkylsulfamoyl, and Me has the abovementioned meaning.

Naphthalocyanines of the formula II in which at least one of the radicals y1 to ye is not hydrogen are of particular interest.

Suitable aminium compounds are, for example, of the formula III

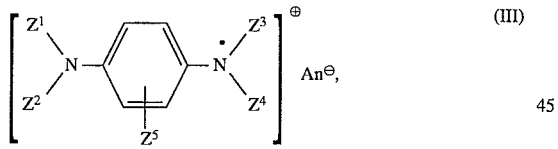

where

Z$^1$ Z$^2$ Z$^3$ and Z$^4$ independently of one another are each C$_1$–C$_{20}$-alkyl which may be interrupted by 1 to 4 oxygen atoms as ether functions, or are each C$_1$–C$_{20}$-alkanoyl or a radical of the formula

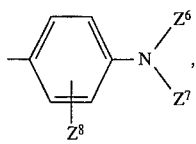

where

Z$^6$ is hydrogen, C$_1$–C$_{20}$-alkyl which may be interrupted by 1 to 4 oxygen atoms as ether functions, or is C$_1$–C$_{20}$-alkanoyl, Z$^7$ is hydrogen or C$_1$–C$_{20}$-alkyl which may be interrupted by 1 to 4 oxygen atoms as ether functions, and Z$^8$ is hydrogen, C$_1$–C$_{20}$-alkyl which may be interrupted by 1 to 4 oxygen atoms as ether functions, or is halogen, and An$^\ominus$ is one equivalent of an anion.

Suitable methine dyes are, for example, of the formula IV

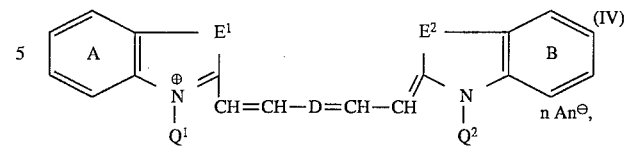

where the rings A and B independently of one another may each be benzofused and may be substituted, E$^1$ and E$^2$ independently of one another are each oxygen, sulfur, imino or a radical of the formula —C(CH$_3$)$_2$— or —CH=CH—, D is a radical of the formula —CE$^3$= or —CH=CE$^3$—CH=,

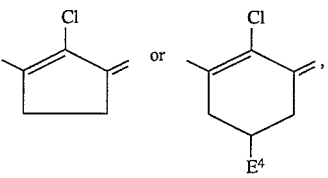

where E$^3$ is hydrogen, C$_1$–C$_6$-alkyl, chlorine or bromine and E$^4$ is hydrogen or C$_1$–C$_6$-alkyl, Q$^1$ and Q$^2$ independently of one another are each phenyl, C$_5$–C$_7$-cycloalkyl, C$_1$–C$_{20}$-alkyl which may be interrupted by 1 to 4 oxygen atoms as ether functions and are unsubstituted or substituted by hydroxyl, chlorine, bromine, carboxyl, C$_1$–C$_4$-alkoxycarbonyl, acryloyloxy, methacryloyloxy, hydroxysulfonyl, C$_1$–C$_7$-alkanoylamino, C$_1$–C$_6$-alkylcarbamoyl, C$_1$–C$_6$-alkylcarbamoyloxy or a radical of the formula G$\oplus$(K)$_3$, where G is nitrogen or phosphorus and K is phenyl, C$_5$–C$_7$-cycloalkyl or C$_1$–C$_{20}$-alkyl, An$^\ominus$ is one equivalent of an anion and n is 1, 2 or 3.

Suitable azulenesquaric acid dyes are, for example, of the formula V

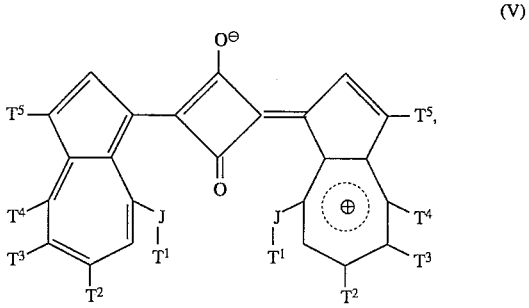

where

J is C$_1$–C$_{12}$-alkylene,

T$^1$ is hydrogen, halogen, amino, hydroxyl, C$_1$–C$_{12}$-alkoxy, phenyl, substituted phenyl, carboxyl, C$_1$–C$_{12}$-alkoxycarbonyl, cyano or a radical of the formula —NT$^7$—CO—T$^6$, —CO—NT$^6$T$^7$ or O—CO—NT$^6$T$^7$, where T$^6$ and T$^7$ independently of one another are each hydrogen, C$_1$—C$_{12}$-alkyl, C$_5$–C$_7$-cycloalkyl, phenyl, 2,2,6,6-tetramethylpiperidin-4-yl or cyclohexylaminocarbonyl, a T$^2$, T$^3$, T$^4$ and T$^5$ independently of one another are each hydrogen or C$_1$–C$_{12}$-alkyl which is unsubstituted or substituted by halogen, amino, $C_1$–$C_{12}$-alkoxy, phenyl, substituted phenyl, carboxyl, $C_1$–$C_{12}$-alkoxycarbonyl or cyano, with the proviso that, when $T^5$ is hydrogen, the ring positions of the substituents J-$T^1$ and $T^4$ may furthermore be interchanged within an azulene ring, on one azulene ring or both azulene rings.

All alkyl, alkylene or alkenyl radicals occurring in the abovementioned formulae may be both straight-chain or branched.

In the formula Ia, II, III or IV, suitable $C_1$–$C_{20}$-alkyl radicals which may be interrupted by 1 to 4 oxygen atoms as ether functions are, for example, methyl, ethyl, propyl, isopropyl, butyl, isobutyl, sec-butyl, tert-butyl, pentyl, isopentyl, neopentyl, tert-pentyl, hexyl, 2-methylpentyl, heptyl, octyl, 2-ethylhexyl, isooctyl, nonyl, isononyl, decyl, isodecyl, undecyl, dodecyl, tridecyl, 3,5,5,7-tetramethylnonyl, isotridecyl (the above names isooctyl, isononyl, isodecyl and isotridecyl are trivial names and originate from the alcohols obtained by the oxo synthesis; cf. Ullmanns Encyklopädie der technischen Chemie, 4th Edition, Volume 7, pages 215 to 217, and Volume 11, pages 435 and 436), tetradecyl, pentadecyl, hexadecyl, heptadecyl, octadecyl, nonadecyl, eicosyl, 2-methoxyethyl, 2-ethoxyethyl, 2-propoxyethyl, 2-isopropoxyethyl, 2-butoxyethyl, 2- or 3-methoxypropyl, 2- or 3-ethoxypropyl, 2- or 3-propoxypropyl, 2- or 3-butoxypropyl, 2or 4-methoxybutyl, 2- or 4-ethoxybutyl, 2- or 4-propoxybutyl, 2or 4-butoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 4,8-dioxadecyl, 3,6,8-trioxadecyl, 3,6,9-trioxaundecyl, 3,6,9,12-tetraoxatridecyl or 3,6,9,12-tetraoxatetradecyl.

In the formula I or II, suitable $C_1$-$C_{20}$-alkyl which is substituted by phenyl is, for example, benzyl or 1- or 2--phenylethyl.

In the formula II, suitable $C_1$-$C_{20}$-alkoxy radicals which may be interrupted by 1 to 4 oxygen atoms as ether functions are, for example, methoxy, ethoxy, propoxy, isopropoxy, butoxy, isobutoxy, pentyloxy, hexyloxy, heptyloxy, octyloxy, 2-ethylhexyloxy, isooctyloxy, nonyloxy, isononyloxy, decyloxy, isodecyloxy, undecyloxy, dodecyloxy, tridecyloxy, isotridecyloxy, tetradecyloxy, pentadecyloxy, hexadecyloxy, heptadecyloxy, octadecyloxy, nonadecyloxy, eicosyloxy, 2-methoxyethoxy, 2-ethoxyethoxy, 2-propoxyethoxy, 2-isopropoxyethoxy, 2-butoxyethoxy, 2- or 3-Methoxypropoxy, 2- or 3-ethoxypropoxy, 2- or 3-propoxypropoxy, 2- or 3-butoxypropoxy, 2- or 4-methoxybutoxy, 2- or 4-ethoxybutoxy, 2- or 4-propoxybutoxy, 2- or 4-butoxybutoxy, 3,6-dioxaheptyloxy, 3,6-dioxaoctyloxy, 4,8-dioxanonyloxy, 3,7-dioxaoctyloxy, 3,7-dioxanonyloxy, 4,7-dioxaoctyloxy, 4,7-dioxanonyloxy, 4,8-dioxadecyloxy, 3,6,8-trioxadecyloxy, 3,6,9-trioxaundecyloxy, 3,6,9,12-tetraoxatridecyloxy or 3,6,9,12-tetraoxatetradecyloxy.

In the formula Ia or V, suitable substituted phenyl is, for example, phenyl which is substituted by $C_1$–$C_6$-alkyl, $C_1$–$C_6$-alkoxy, hydroxyl or halogen. As a rule, from 1 to 3 substituents may occur.

Halogen in formula Ib, II, III or V is, for example, fluorine, chlorine or bromine.

W in the formula Ia or II and $X^2$ or $X^3$ in the formula Ib are, for example, methylimino, ethylimino, propylimino, isopropylimino or butylimino.

$R^1$ to $R^{16}$ in the formula Ia and $Y^9$ to $Y^{12}$ in the formula II are, for example, dimethylsulfamoyl, diethylsulfamoyl, dipropylsulfamoyl, dibutylsulfamoyl or N-Methyl-N-ethylsulfamoyl.

$C_5$–$C_7$-Cycloalkyl in the formula Ia or II is, for example, cyclopentyl, cyclohexyl, methylcyclohexyl or cycloheptyl.

$C_2$–$C_{20}$-Alkenyl and $C_4$–$C_{20}$-alkadienyl in the formula II is, for example, vinyl, allyl, prop-1-en-1-yl, methallyl, ethallyl, but-3-en-1-yl, pentenyl, pentadienyl, hexadienyl, 3,7-dimethylocta-1,6-dien-1-yl, undec-10-en-1 -yl, 6,10-methylundeca-5,9-dien-2-yl, octadec-9-en-1-yl, octadeca-9,12-dien-1-yl, 3,7,11,15-tetramethylhexadec-1-en-3-yl or eicos-9-en-1-yl.

$C_3$–$C_{20}$-Alkenyloxy in the formula Ia is, for example, allyloxy, methallyloxy, but-3-en-1-yloxy, pentenyloxy, undec-10-en-1-yloxy, octadec-9-en-1-yloxy or eicos-9-en-1-yloxy.

$Z^6$ in the formula III is, for example, formyl, acetyl, propionyl, butyryl, isobutyryl, pentanoyl, hexanoyl, heptanoyl, octanoyl or 2-ethylhexanoyl.

When the rings A and/or B in the formula IV are substituted, suitable substituents are, for example, $C_1$–$C_6$-alkyl, phenyl-$C_1$–$C_6$-alkoxy, phenoxy, halogen, hydroxyl, amino, $C_1$–$C_6$-mono- or dialkylamino or cyano. The rings are, as a rule, monosubstituted, disubstituted or trisubstituted.

$E^3$ and $E^4$ in the formula IV are, for example, methyl, ethyl, propyl, isopropyl, butyl, isobutyl, sec-butyl, pentyl, isopentyl, neopentyl, tert-pentyl or hexyl.

$Q^1$ and $Q^2$ in the formula IV are, for example, IV cyclopentyl, cyclohexyl, 2-methoxyethyl, 2-ethoxyethyl, 2- or 3-methoxypropyl, 2- or 3-ethoxypropyl, 2-hydroxyethyl, 2- or 3-hydroxypropyl, -chloroethyl, 2-bromoethyl, 2- or 3-chloropropyl, 2- or 3-bromopropyl, 2-carboxyethyl, 2- or 3-carboxypropyl, 2-methoxycarbonylethyl, 2-ethoxycarbonylethyl, 2- or 3-methoxycarbonylpropyl, 2or 3-ethoxycarbonylpropyl, 2-acryloyloxyethyl, 2- or 3-acryloyloxypropyl, 2-methacryloyloxyethyl, 2- or 3-methacryloyloxypropyl, 2-hydroxysulfonylethyl, 2- or 3-hydroxysulfonylpropyl, 2-acetylaminoethyl, 2- or 3-acetylaminopropyl, 2-methylcarbamoylethyl, 2-ethylcarbamoylethyl, 2- or 3-methylcarbamoylpropyl, 2- or 3-ethylcarbamoylpropyl, 2-methylcarbamoyloxyethyl, 3-ethylcarbamoyloxyethyl, 2- or 3-methylcarbamoyloxypropyl, 2-or 3-ethylcarbamoyloxypropyl, 2-(trimethylammonium)ethyl 3-(triethylammonium)ethyl, 2- or 3-(trimethylammonium)propyl, 2or 2-(triethylammonium)propyl, 2-(triphenylphosphonium)ethyl or 2- or 3-(triphenylphosphonium)propyl.

An⊖ in the formula III or IV is derived, for example, from anions of organic or inorganic acids. For example, methansulfonate, 4-methylbenzenesulfonate, acetate, trifluoroacetate, heptafluorobutyrate, chloride, bromide, iodide, perchlorate, tetrafluoroborate, nitrate, hexafluorophosphate and tetraphenylborate are particularly preferred.

J in the formula V is, for example, methylene, ethylene, 1,2- or 1,3-propylene, 1,2-, 1,3-, 2,3- or 1,4-butylene, pentamethylene, hexamethylene, heptamethylene, octamethylene, nonamethylene, decamethylene, undecamethylene or dodecamethylene.

$T^2$, $T^3$, $T^4$ and $T^5$ in the formula V are, for example, methyl, ethyl, propyl, isopropyl, butyl, isobutyl, sec-butyl, tert-butyl, pentyl, isopentyl, neopentyl, tert-pentyl, 2-methylbutyl, hexyl, 2-methylpentyl, heptyl, octyl, 2-ethylhexyl, isooctyl, nonyl, isononyl, decyl, undecyl, dodecyl, fluoromethyl, chloromethyl, difluoromethyl, trifluoromethyl, trichloromethyl, 2-fluoroethyl, 2-chloroethyl, 2-bromomethyl, 1,1,1-trifluoroethyl, heptafluoropropyl, 4-chlorobutyl, 5-fluoropentyl, 6-chlorohexyl, cyanomethyl, 2-cyanoethyl, 3-cyanopropyl, 2-cyanobutyl, 4-cyanobutyl, 5-cyanopentyl, 6-cyanohexyl, 2-aminoethyl, 2-aminopropyl, 3-aminopropyl, 2-aminobutyl, 4-aminobutyl, 5-aminopentyl, 6-aminohexyl, 2-hydroxyethyl, 2-hydroxypropyl, 3-hydroxypropyl, 2-hydroxybutyl, 4-hydroxybutyl, 5-hydroxypentyl, 6-hydroxyhexyl, 2-methoxyethyl, 2-ethoxyethyl, 2-propoxyethyl, 2-isopropoxyethyl, 2-butoxyethyl, 2-methoxypropyl, 2-ethoxypropyl, 3-ethoxypropyl, 4-ethoxybutyl, 4-isopropoxybutyl, 5-ethoxypentyl, 6-methoxyhexyl, benzyl, 1-phenylethyl, 2-phenylethyl, 4-chlorobenzyl, 4-methoxybenzyl, 2-(4-methylphenyl)ethyl, carboxymethyl, 2-carboxyethyl, 3-carboxypropyl, 4-carboxybutyl, 5-carboxypentyl, 6-carboxyhexyl, methoxycarbonylmethyl, ethoxycarbonylmethyl, 2-methoxycarbonylethyl, 2-ethoxycarbonylethyl, 3-methoxycarbonylpropyl, 3-ethoxycarbonylpropyl, 4-methoxycarbonylbutyl, 4-ethoxycarbonylbutyl, 5-methoxycarbonylpentyl, 5-ethoxycarbonylpentyl, 6-methoxycarbonylhexyl or 6-ethoxycarbonylhexyl.

$T^1$ in the formula V is, for example, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, tert-pentyloxycarbonyl, hexyloxycarbonyl, heptyloxycarbonyl, octyloxycarbonyl, isooctyloxycarbonyl, nonyloxycarbonyl, isononyloxycarbonyl, decyloxycarbonyl, isodecyloxycarbonyl, undecyloxycarbonyl, dodecyloxycarbonyl, methoxy, ethoxy, propoxy, isopropoxy, butoxy, isobutoxy, pentyloxy, hexyloxy, acetylamino, carbamoyl, mono- or dimethylcarbamoyl, mono- or diethylcarbamoyl, monocyclohexylcarbonyl, phenylcarbamoyl, dimethylcarbamoyloxy or diethylcarbamoyloxy.

The novel use of compounds which originate from the class consisting of the metal-free or metal-containing naphthalocyanines is preferred.

The novel use of naphthalocyanines of the formula IIa

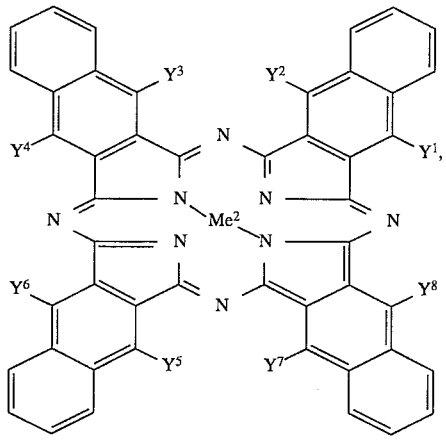

(IIa)

where $Y^1$, $Y^2$, $Y^3$, $Y^4$, $Y^5$, $Y^6$, $Y^7$ and $Y^8$ independently of one another are each hydrogen, hydroxyl, $C_1$–$C_4$-alkyl or $C_1$–$C_{20}$-alkoxy and $Me^2$ is two hydrogen atoms, two lithium atoms, magnesium, zinc, manganese, VO, AlCl or a radical

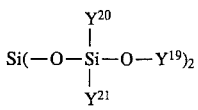

where $Y^{19}$ is $C_1$–$C_{13}$-alkyl or $C_{10}$–$C_{20}$-alkadienyl and $U_{20}$ and $Y_{21}$ independently of one another are each $C_1$–$C_{13}$-alkyl or $C_2$–$C_4$-alkenyl,
is noteworthy.

The novel use of naphthalocyanines of the formula IIa, where $Y^1$, $Y^2$, $Y^3$, $Y^4$, $Y^5$, $Y^6$, $Y^7$ and $Y^8$ independently of one another are each hydroxyl, $C_1$–$C_{20}$-alkoxy, in particular $C_1$–$C_{10}$-alkoxy, is particularly noteworthy. The alkoxy radicals may be identical or different.

The novel use of naphthalocyanines of the formula IIa, where $Me^2$ is two hydrogen atoms, is also particularly noteworthy.

The phthalocyanines of the formula Ia are known per se and are described, for example, in DE-B-1 073 739 or EP-A-155 780 or can be obtained by methods known per se, as used in the preparation of phthalocyanines or naphthalocyanines and as described, for example, in F. H. Moser and A. L. Thomas "The Phthalocyanines", CRC Press, Boca Rota, Fla, 1983, or J. Am. Chem. Soc. 106 (1984), 7404–7410. The phthalocyanines of the formula Ib are likewise known per se and described, for example, in EP-A-155 780 or can be obtained by the methods of the abovementioned prior art (Moser, J. Am. Chem. Soc.).

The naphthalocyanines of the formula II are likewise known per se and are described, for example, in EP-A-336 213, EP-A-358 080, GB-A-2 168 372 or GB-A-2 200 650 or can be obtained by the methods of the abovementioned prior art (Moser, J. Am. Chem. Soc.).

The aminium compounds of the formula III are likewise known per se and are described, for example, in U.S. Pat. No. 3,484,467 or can be obtained by the methods stated there.

The methine dyes of the formula IV are likewise known per se and are described, for example, in EP-A-464 543 or can be obtained by the methods stated there.

The azulenesquaric acid dyes of the formula V are likewise known per se and are described, for example, in EP-A-310 080 or U.S. Pat. No. 4,990,649 or can be obtained by the methods stated there.

For use as crack-detecting agents, the abovementioned compounds are generally used in the form of solutions. Suitable solvents are organic solvents. Aromatic hydrocarbons, such as toluene, xylene, dodecylbenzene, diisopropylnaphthalene, liquid paraffin or a mixture of higher aromatics which is commercially available under the name Shellsol®AB (from Shell), are preferably used. If required, nonionic surfactants, for example alkylphenol polyethylene glycol ethers, are also added in minor amounts (for example up to 15% by weight, based on the weight of solution). In order to avoid an excessively high viscosity of the resulting solutions, a concentration of the compound which absorbs IR radiation and fluorescence in the IR range is generally chosen to be from 2 to 50% by weight, based on the weight of the solution.

Suitable materials in which a possible crack is to be detected are, for example, articles consisting of metal, such as iron alloys, aluminum alloys, silicon alloys, titanium alloys or magnesium alloys, ceramic materials based on silica or alumina, or plastics, such as polyolefins (eg. polyethylene or polypropylene), polycarbonate, polymethyl (meth)acrylate, polyurethane, polyester or polymers based on acrylic acid, butadiene and styrene.

The testing for cracks is carried out, as a rule, by degreasing and cleaning the test specimen and then coating it with the solution described in detail above. Excess test solution is then removed and the test specimen is then cleaned with water and dried.

For detection, the fluorescence of the crack-detecting agent is advantageously excited by means of a semiconductor laser or a semiconductor diode. It is particularly advantageous to use a semiconductor laser or semiconductor diode having a wavelength of the maximum emission in the spectral range of $\lambda_{max}$−100 nm to $\lambda_{max}$+20 nm. $\lambda_{max}$ is the wavelength of the absorption maximum of the marking substance. The wavelength of the maximum emission is from 620 to 1,200 nm.

The fluorescent light thus produced is advantageously detected by means of a semiconductor detector, in particular a silicon photodiode or germanium photodiode.

The detection is carried out particularly advantageously if an interference filter and/or or an edge filter (having a short-wavelength transmission edge in the range from $\lambda_{max}$ to $\lambda_{max}+80$ nm) and/or a polarizer is also present in front of the detector.

The advantage of the compounds used according to the invention as crack-detecting agents is that they are easy to detect even in the presence of daylight. No expensive lamps are required, and darkened special inspection boxes can be dispensed with.

Furthermore, there is no interference from visible fluorescence, which may occur, for example, in the case of plastics parts or articles which contain dyes. The compounds used according to the invention are therefore also suitable as crack-detecting agents for coated articles.

When a suitable video camera is used as a detector for the NIR fluorescence and digital image processing is employed, the crack detection can also be automated.

The examples which follow illustrate the invention.

a) Preparation of the test solution

A test solution was prepared by mixing 25 g of xylene, 25 g of a high-boiling mixture of aromatics (commercially available under the name Shellsol® AB from Shell), 40 g of white liquid paraffin, 20 g of nonionic surfactant based on alkylphenol polyethylene glycol ethers and 0.1 g of a detector compound defined below.

b) Preparation of the test specimen

The test specimen used was an aluminum block which had several cracks.

For sample preparation, the test solution was applied with a brush to the degreased and cleaned test specimen. It was allowed to act for 10 minutes, after which the excess test solution was wiped off with a paper cloth and the test specimen was washed under running water and dried.

In some cases designated below, the test specimen was then also sprayed with a commercially available developer based on silicon dioxide.

c) Detection method 1

The test specimen was illuminated over its entire surface with a tungsten/halogen lamp or a semiconductor diode laser (20 mW, 820 nm).

The fluorescence of the detector compound was observed with a black-and-white video camera (CCD 330 SW/RS from Spindler and Hoyer), which was equipped with a lens and an interference filter (890 nm). The distribution of the detector compound over the surface was obtained as an image on a black-and-white monitor from Sony.

d) Detection method 2

The test specimen was scanned with the focussed beam of a semiconductor diode laser (20 mW, 820 nm).

The fluorescence was observed as described under c).

The following dyes were used as detector compounds.

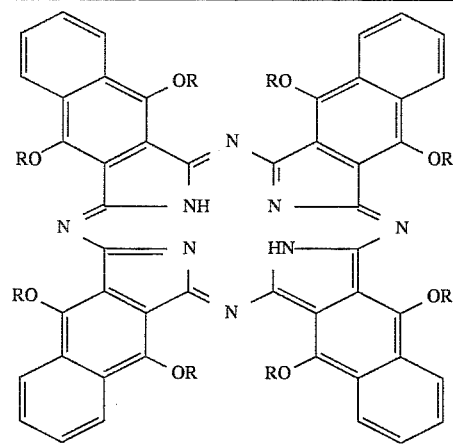

Dye 1
R = n-$C_4H_9$
Dye 2
R = n-$C_5H_{11}$
Dye 3
R = n-$C_{12}H_{25}$

-continued
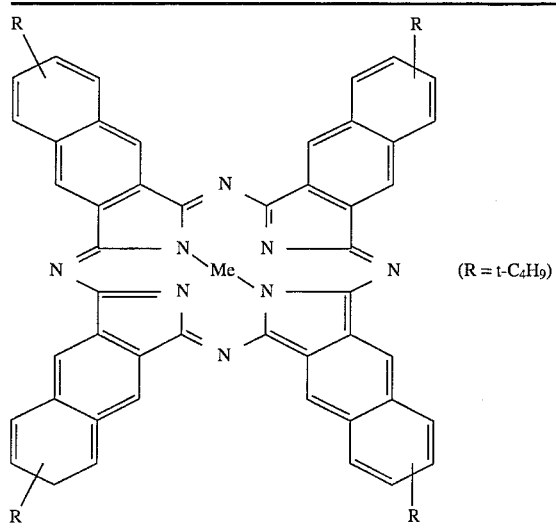
(R = t-C₄H₉)
Dye 4
Me = 2H
Dye 5
Me = Zn
Dye 6
Me = AlC
Dye 7
NcSi[—O—Si(CH₃)₂—O—C₁₂H₂₅]₂  (Nc = naphthalocyanine)
Dye 8
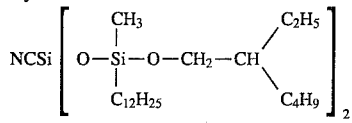
Dye 9
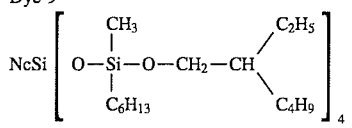
Dye 10
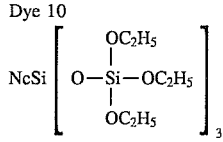
Dye 11
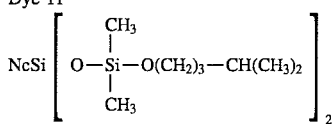
Dye 12
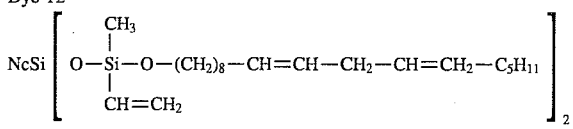
Dyes 13 to 15

-continued

| Dye No. | Z | An⊖ |
|---|---|---|
| 13 | $C_4H_9$ | $NO_3^\ominus$ |
| 14 | $C_2H_5$ | $NO_3^\ominus$ |
| 15 | $C_4H_9$ | $BF_4^\ominus$ |

Dyes 16 to 20

| Dye No. | $Q^1$ | $Q^2$ | $Q^3$ | $Q^4$ | An⊖ |
|---|---|---|---|---|---|
| 16 | $CH_3$ | $CH_3$ | Cl | Cl | $I^\ominus$ |
| 17 | $CH_3$ | $CH_3$ | H | H | $I^\ominus$ |
| 18 | $C_2H_4OCNHC(CH_3)_3$ (O) | $C_2H_4OCNHC(CH_3)_3$ (O) | H | H | $I^\ominus$ |
| 19 | $C_2H_4CNHC_6H_{13}$ (O) | $C_2H_4CNHC_6H_{13}$ (O) | H | H | $ClO_4^\ominus$ |
| 20 | $C_3H_6SO_3^\ominus$ | $C_3H_6SO_3H$ | H | H | betaine |

Dye No. 21

When detection method 1 was used, all cracks (independently of the presence of daylight) were detectible in the pre-treated test specimens (without developer) from a weak fluorescence.

When the test specimens were also treated with developer, all cracks (independently of the presence of daylight) were detectible from a strong fluorescence.

When detection method 2 was used, all cracks (independently of the presence of daylight) were detectible in the pre-treated test specimens (without developer) from a strong fluorescence contrast.

We claim:

1. A method for detecting cracks in a material, comprising applying to said material a solution of a crack-detecting agent having an absorption maximum in the range from 600 to 1,200 nm and a fluorescence maximum in the range from 620 to 1,200 nm, and exciting said applied solution of the crack-detecting agent to render it fluorescent to thereby detect any cracks present in said material, wherein said crack-detecting agent is of the following formulas Ia, Ib, II, III, IV or V:

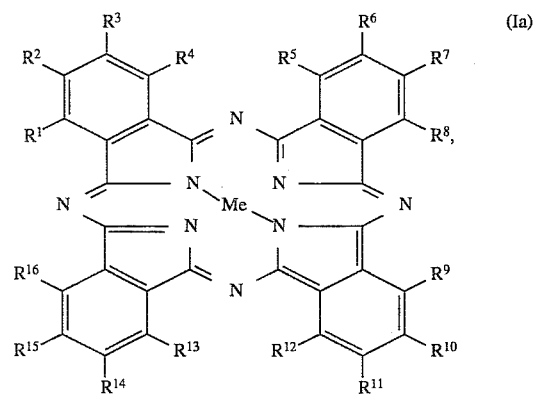

-continued

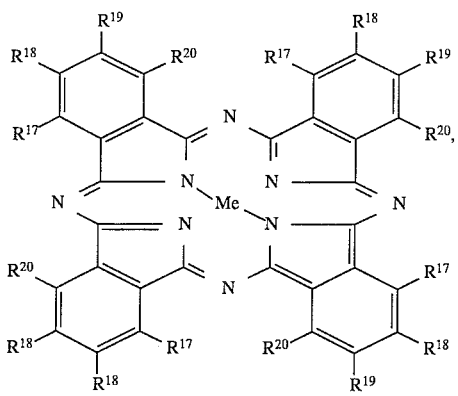
(Ib)

where

Me¹ is two lithium atoms, magnesium, zinc, manganese, VO, tiO, AlCl or a radical of the formula

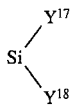

where $Y^{17}$ and $Y^{18}$ independently of one another are each hydroxyl, $C_1$–$C_{20}$-alkoxy, $C_1$–$C_{20}$-alkyl, $C_2$–$C_{20}$-alkenyl, $C_3$–$C_{20}$-alkenyloxy or a radical of the formula

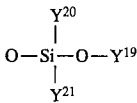

where $Y^{19}$ is $C_1$–$C_{20}$-alkyl, $C_2$–$C_{20}$-alkenyl or $C_4$–$C_{20}$-alkadienyl and $Y^{20}$ and $Y^{11}$ independently of one another are each $C_1$–$C_{12}$-alkyl, $C_2$–$C_{12}$-alkenyl or the above-defined radical $OY^{19}$, at least 4 of the radicals $R^1$ to $R^{16}$ independently of one another are each a radical of the formula W—$X^1$, where W is a chemical bond, oxygen, sulfur, imino, $C_1$–$C_4$-alkylimino or phenylimino and $X^1$ is $C_1$–$C_{20}$-alkyl which may be interrupted by 1 to 4 oxygen atoms as ether functions and may be substituted by phenyl, or $X^1$ is adamantyl, $C_5$–$C_7$-cycloalkyl or unsubstituted or substituted phenyl, any remaining radicals $R^1$ to $R^{16}$ are each hydrogen, halogen, hydroxysulfonyl or $C_1$–$C_4$-dialkylsulfamoyl, $R^{17}$ and $R^{18}$ or $R^{18}$ and $R^{19}$ or $R^{19}$ and $R^{20}$ together in each case form a radical of the formula $X^2$—$C_2H_4$—$X^3$, where one of the two radicals $X^2$ and $X^3$ is oxygen and the other is imino or $C_1$–$C_4$-alkylimino, and $R^{19}$ and $R^{20}$ or $R^{17}$ and $R^{20}$ or $R^{17}$ and $R^{18}$ independently of one another are in each case hydrogen or halogen,

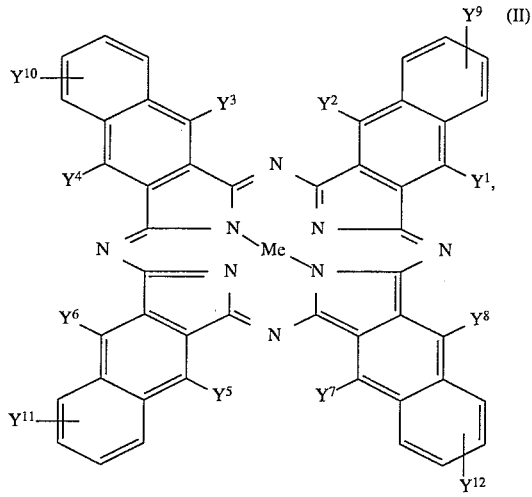
(II)

where $Y^1$, $Y^2$, $Y^3$, $Y^4$, $Y^5$, $Y^6$, $Y^7$ and $Y^8$ independently of one another are each hydrogen, hydroxyl or a radical of the formula W—$X^4$, where W is a chemical bond, oxygen sulfur, imino, $C_1$–$C_4$-alkylimino or phenylimino and $X^4$ is $C_1$–$C_{20}$-alkyl, which may be interrupted by 1 to 4 oxygen atoms as ether functions and may be substituted by phenyl, or $X^4$ is $C_5$–$C_7$-cycloalkyl, $C_2$–$C_{20}$-alkenyl or $C_4$–$C_{20}$-alkadienyl, and $Y^9$, $Y^{10}$, $Y^{11}$ and $Y^{12}$ independently of one another are each hydrogen, $C_1$–$C_{20}$-alkyl or $C_1$–$C_{20}$-alkoxy, where the alkyl groups may each be interrupted by 1 to 4 oxygen atoms as ether functions, or are each halogen, hydroxysulfonyl or $C_1$–$C_4$-dialkylsulfamoyl, and Me² is two hydrogen atoms or has the above-defined meaning of Me¹,

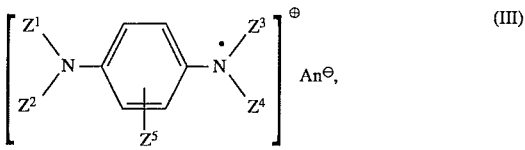
(III)

where $Z^1$, $Z^2$, $Z^3$ and $Z^4$ independently of one another are each $C_1$–$C_{20}$-alkyl which may be interrupted by 1 to 4 oxygen atoms as ether functions, or are each $C_1$–$C_{20}$-alkanoyl or a radical of the formula

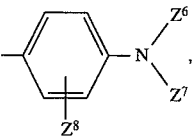

where $Z^6$ is hydrogen, $C_1$–$C_{20}$-alkyl which may be interrupted by 1 to 4 oxygen atoms as ether functions, or is $C_1$–$C_{20}$-alkanoyl, $Z^7$ is hydrogen or $C_1$–$C_{20}$-alkyl which may be interrupted by 1 to 4 oxygen atoms as ether functions, and $Z^8$ is hydrogen, $C_1$–$C_{20}$-alkyl which may be interrupted by 1 to 4 oxygen atoms as ether functions, or is halogen, and An⊖ is one equivalent of an anion,

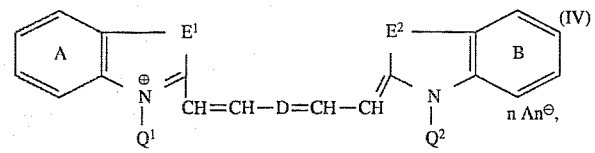

where the rings A and B independently of one another may each be benzofused and may be substituted,
$E^1$ and $E^2$ independently of one another are each oxygen, sulfur, imino or a radical of the formula —C(CH$_3$)$_2$— or —CH=CH—, D is a radical of the formula —CE$^3$= or —CH=CE$^3$—CH=,

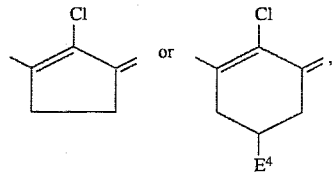

where $E^3$ is hydrogen, $C_1$–$C_6$-alkyl, chlorine or bromine and $E^4$ is hydrogen or $C_1$–$C_6$-alkyl, $Q^1$ and $Q^2$ independently of one another are each phenyl, $C_5$–$C_7$-cycloalkyl, $C_1$–$C_{20}$-alkyl which may be interrupted by 1 to 4 oxygen atoms as ether functions and are unsubstituted or substituted by hydroxyl, chlorine, bromine, carboxyl, $C_1$–$C_4$-alkoxy-carbonyl, acryloyloxy, methacryloyloxy, hydroxysulfonyl, $C_1$–$C_7$-alkanoylamino, $C_1$–$C_6$-alkylcarbamoyl, $C_1$–$C_6$-alkylcarbamoyloxy or a radical of the formula G⊖ (K)$_3$, where G is nitrogen or phosphorus and K is phenyul, $C_5$–$C_7$-cycloalkyl or $C_1$–$C_{20}$-alkyl, An⊖ is one equivalent of an anion and n is 1, 2 or 3,

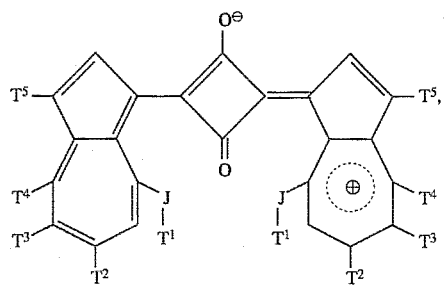

where

J is $C_1$–$C_{12}$-alkylene, $T^1$ is hydrogen, halogen, amino, hydroxyl, $C_1C_{12}$-alkoxy, phenyl, substituted phenyl, carboxyl, $C_{11}$–$C_{12}$-alkoxycarbonyl, cyano or a radical of the formula —NT$^7$—CO—T$^6$, —CO—NT$^6$T$^7$ or O —CO—NT$^6$T$^7$, where $T^6$ and $T^7$ independently of one another are each hydrogen, $C_1$–$C_{12}$alkyl, $C_5$–$C_7$-cycloalkyl, phenyl, 2,2,6,6-tetramethylpiperidin-4-yl or cyclohexylaminocarbonyl, and $T^2$, $T^3$, $T^4$ and $T^5$ independently of one another are each hydrogen or $C_1$–$C_{12}$-alkyl which is unsubstituted or substituted by halogen, amino, $C_1$–$C_{12}$-alkoxy, phenyl, substituted phenyl, carboxyl, $C_1$–$C_{12}$-alkoxycarbonyl or cyano, with the proviso that, when $T^5$ is hydrogen, the ring positions of the substituents J-$T^1$ and $T^4$ may furthermore be interchanged within an azulene ring, on one azulene ring or both azulene rings.

2. The method according to claim 1, wherein the crack-detecting agent of formula II is of the following formula IIa

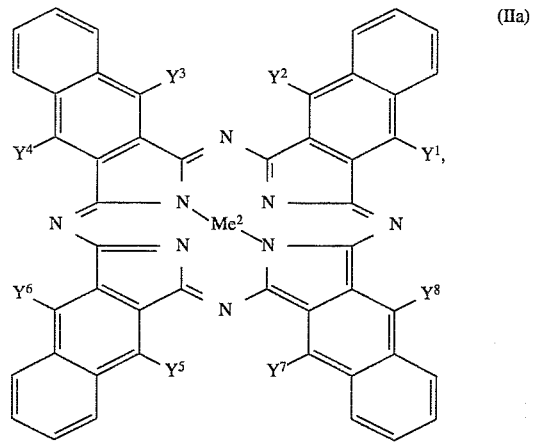

where $Y^1$, $Y^2$, $Y^3$, $Y^4$, $Y^5$, $Y^6$, $Y^7$ and $Y^8$ independently of one another are each hydrogen, hydroxyl, $C_1$–$C_4$-alkyl or $C_1$–$C_{20}$-alkoxy and $Me^2$ is two hydrogen atoms, two lithium atoms, magnesium, zinc, manganese, VO, AlCl or a radical

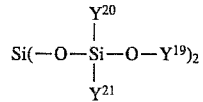

where $Y^{19}$ is $C_1$–$C_{13}$-alkyl or $C_{10}$–$C_{20}$-alkadienyl and $Y^{20}$ and $Y^{21}$ independently of one another are each $C_1$–$C_{13}$-alkyl or $C_2$–$C_4$-alkenyl.

3. The method according to claim 1, wherein the crack-detecting agent is excited by means of a semiconductor laser or a semiconductor diode having a maximum emission in the spectral range of $\lambda_{max}$–100 nm to $\lambda_{max}$+20 rim, wherein $\lambda_{max}$ is the wavelength of the absorption maximum of the crack-detecting agent.

4. The method according to claim 3, wherein any cracks present are detected by means of a semiconductor detector.

5. The method according to claim 4, wherein an interference filter, an edge filter, or both, optionally also a polarizer are present in front of said detector.

* * * * *